United States Patent
Jiang et al.

(10) Patent No.: US 11,566,181 B2
(45) Date of Patent: Jan. 31, 2023

(54) PROCESS FOR PRODUCING SURFACTANT HAVING TWO HEAD GROUPS AND A SINGLE TAIL GROUP PER MOLECULE

(71) Applicant: Tarim University, Xinjiang (CN)

(72) Inventors: Jianhui Jiang, Xinjiang (CN); Yuan Zhang, Xinjiang (CN); Yuhui Liu, Xinjiang (CN); Shiwei Jiang, Xinjiang (CN); Fei Ren, Xinjiang (CN); Yanxia Yang, Xinjiang (CN); Shaozhen Qi, Xinjiang (CN)

(73) Assignee: TARIM UNIVERSITY, Xinjiang (CN)

( * ) Notice: Subject to any disclaimer, the term of this patent is extended or adjusted under 35 U.S.C. 154(b) by 89 days.

(21) Appl. No.: 17/366,879

(22) Filed: Jul. 2, 2021

(65) Prior Publication Data

US 2022/0080370 A1 Mar. 17, 2022

(30) Foreign Application Priority Data

Sep. 11, 2020 (CN) .......................... 202010952329.3

(51) Int. Cl.
| | | |
|---|---|---|
| C07C 327/18 | (2006.01) | |
| C09K 23/00 | (2022.01) | |
| C07C 51/353 | (2006.01) | |
| C07C 67/08 | (2006.01) | |
| C07C 303/16 | (2006.01) | |
| C07C 329/16 | (2006.01) | |

(52) U.S. Cl.
CPC ............ *C09K 23/00* (2022.01); *C07C 51/353* (2013.01); *C07C 67/08* (2013.01); *C07C 303/16* (2013.01); *C07C 327/18* (2013.01); *C07C 329/16* (2013.01)

(58) Field of Classification Search
CPC ....... C09K 23/00; G01S 17/894; G01S 7/481; G06T 2207/20024; G06T 5/20; G06T 7/11; H04N 5/35581; C07C 303/02; C07C 303/16; C07C 309/17; C07C 327/18; C07C 329/16; C07C 51/353; C07C 51/363; C07C 53/19; C07C 67/08; C07C 69/63

See application file for complete search history.

(56) References Cited

FOREIGN PATENT DOCUMENTS

CN 106588708 * 4/2017

OTHER PUBLICATIONS

Metia et al. (Studies on the Preparation of Quaternary Ammonium Biocide α-Dmethylamino Palmitic Acid Ethyl Ester Methobromide—Part I, Fertilizer Technology, vol. 20 Nos. 1-4, pp. 1-5, Published Dec. 1983) (Year: 1983).*

* cited by examiner

*Primary Examiner* — Yevgeny Valenrod
*Assistant Examiner* — Blaine G Doletski
(74) *Attorney, Agent, or Firm* — Panitch Schwarze Belisario & Nadel LLP

(57) ABSTRACT

A process for producing a surfactant having two head groups and a single tail group per molecule, including steps of: producing a compound of Formula (1) from ethanol and carbon disulfide; producing a compound of Formula (2) from a carboxylic acid and bromine; producing a compound of Formula (3) from the compound of Formula (2) and methanol; producing a compound of Formula (4) from the compound of Formula (1) and the compound of Formula (3); and producing a compound of Formula (5) from the compound of Formula (4) by a direct oxidation process or by a peracid oxidation process. The surfactant produced by the process has lower critical micelle concentration and enables a lower surface tension of a liquid as compared with prior surfactants with two head groups per molecule, thereby enabling the amount of surfactant required and thus the cost to be substantially reduced.

9 Claims, No Drawings

PROCESS FOR PRODUCING SURFACTANT HAVING TWO HEAD GROUPS AND A SINGLE TAIL GROUP PER MOLECULE

CROSS REFERENCE TO RELATED APPLICATION

This patent application claims the benefit and priority of Chinese Patent Application No. 202010952329.3 filed on Sep. 11, 2020, the disclosure of which is incorporated by reference herein in its entirety as part of the present application.

TECHNICAL FIELD

The present disclosure is related to the field of surfactant production, and, in particular, to a process for producing a surfactant having two head groups and a single tail group per molecule.

BACKGROUND ART

Surfactants have found wide use in scientific research and industrial applications and have great significance due to their self-organized behavior and abilities to reduce surface tension of aqueous solutions, as a result of their asymmetrical molecular structure. Decreasing electrostatic repulsion between hydrophilic head groups of the surfactant molecules and repulsion between hydration layers has the effect of promoting a more dense arrangement of the surfactant molecules in their self-organized structure, causing the surfactants to exhibit an effectively improved surface activity. If the surfactant molecules are sparsely arranged at a liquid-air interface, a portion of methylene groups (not methyl terminal groups of the carbon chain) of the surfactant molecules may occupy a part of the area of the air side of the interface due to tilting of the carbon chain of the surfactant molecules at the interface; while if the surfactant molecules are densely arranged in an upright manner at a liquid-air interface, the air side of the interface may be composed mainly of methyl terminal groups of the carbon chain of the surfactant molecules. Practice shows that the latter may lower the surface tension of water to a greater extent.

Since the surfactants play a large role in industrial and agriculture productions and daily life, improvement of their surface activities has always been a major focus for the practical application. Conventionally, both electrostatic repulsion between hydrophilic head groups of the surfactant molecules and repulsion between hydration layers may be decreased by physical methods, for example, by addition of inorganic salts and by increasing the temperature of the aqueous solutions, respectively. Also, as another conventional physical method, the attraction between the head groups of surfactants is used to promote the interaction of them, for example, by using a composition of cationic and anionic surfactants. However, these physical methods suffer from certain limitations. As an example, the composition of cationic and anionic surfactants can improve the surface activity of the aqueous solution to some extent, but the stability of the aqueous solution may be deteriorated, easily causing precipitates to be produced, due to the fact that ion head groups of the cationic and anionic surfactant molecules with a ratio of 1:1 are electrically neutralized. So, generalized application of the physical methods is limited.

The applicant has already proposed a method for synthesizing a Gemini surfactant which exhibits good surface activity (see Chinese patent application publication No. CN 106588708 A). However, it has been found in practice that, due to limitations in a critical micelle concentration (CMC), the used amount of the surfactant is large, thereby leading to a high cost.

SUMMARY

Therefore, an objective of the present disclosure is to provide a process for producing a surfactant having two head groups and a single tail group per molecule, which allows a reduced amount to be used and thus a reduced cost.

Accordingly, an objective of the disclosure is realized by a process for producing a surfactant having two head groups and a single tail group per molecule, comprising steps of:

a. producing a compound of Formula (1) from ethanol and carbon disulfide ($CS_2$) according to the following chemical equation (I):

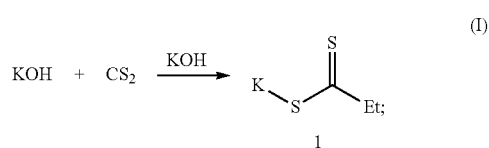

b. producing a compound of Formula (2) from a carboxylic acid and bromine ($Br_2$) according to the following chemical equation (II):

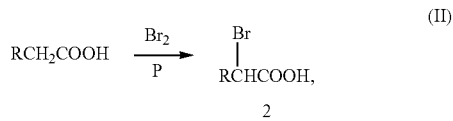

where, R is C12, C14, C16, or C18 alkyl;

c. producing a compound of Formula (3) from the compound of Formula (2) and methanol according to the following chemical equation (III):

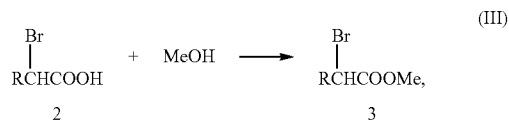

where, R is C12, C14, C16, or C18 alkyl;

d. producing a compound of Formula (4) from the compound of Formula (1) and the compound of Formula (3) according to the following chemical equation (IV):

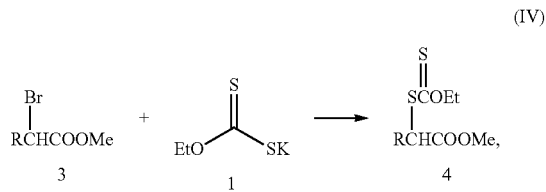

where, R is C12, C14, C16, or C18 alkyl; and e. producing a compound of Formula (5) from the compound of Formula (4) by a direct oxidation process or by a peracid oxidation process according to the following chemical equation (V):

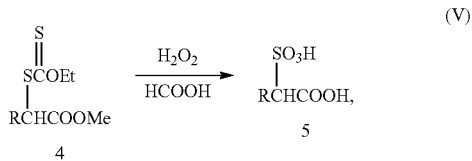

where, R is C12, C14, C16, or C18 alkyl;

wherein, the compound of Formula (5) obtained is subjected to neutralization treatment with sodium hydroxide (NaOH) so as to obtain a surfactant having two head groups and a single tail group per molecule.

The step (a) may comprise: introducing ethanol and $CS_2$ into a reaction vessel, which is then placed in an ice bath; adding thereto a 5 mol/L aqueous solution of potassium hydroxide (KOH) while stirring, with the stirring further continued after the addition; and subjecting the resulting reaction mixture to solvent removal through rotary evaporation and recrystallization from anhydrous ethanol to give the compound of Formula (1), i.e., potassium xanthate.

As a particular example, the step (a) may comprise: introducing 6 mL of $CS_2$ and 50 mL of ethanol into a 150 mL round bottomed flask, which is then placed in an ice bath; adding thereto 20 mL of a 5 mol/L aqueous solution of KOH while stirring, with the stirring further continued for 1.5 hours after the addition; and subjecting the resulting reaction mixture to solvent removal through rotary evaporation and recrystallization from anhydrous ethanol to give the compound of Formula (1), i.e., potassium xanthate.

The step (b) may comprise: adding red phosphorus into a carboxylic acid to form a mixture, which is then heated at 95.9° C.; adding bromine dropwise to the mixture while being heated and stirred, with the mixture further continually heated at 95.9° C. and stirred after the addition; adding water to the mixture, with the mixture further continually stirred for 20 minutes after the addition of water, to give a reaction product; and subjecting the reaction product to be extracted with ether, washed once with each of distilled water and brine, dried over anhydrous magnesium sulfate ($MgSO_4$), concentrated under reduced pressure, and recrystallized from hexane to obtain the compound of Formula (2). The carboxylic acid has a general formula of $RCH_2COOH$, where R is C12, C14, C16, or C18 alkyl.

As a particular example, the step (b) may comprise: adding 311 mg of red phosphorus to 7.73 mmol of a carboxylic acid to form a mixture, which is then heated at 95.9° C.; adding 4.9 g of bromine dropwise to the mixture while being heated and stirred, with the mixture further continually heated at 95.9° C. and stirred for 6 hours after the addition; adding water to the mixture, with the mixture further continually stirred for 20 minutes after the addition of water, to give a reaction product; and subjecting the reaction product to be extracted with ether, washed once with each of distilled water and brine, dried over anhydrous $MgSO_4$, concentrated under reduced pressure, and recrystallized from hexane to obtain the compound of Formula (2).

The step (c) may comprise: subjecting the compound of Formula (2) to a reaction with anhydrous methanol at room temperature for 16 hours under nitrogen atmosphere; and removing methanol from the resulting reaction mixture under a vacuum to obtain the compound of Formula (3).

The step (d) may comprise: introducing acetone and then the compound of Formula (3) into a reaction vessel, which is then placed in an ice bath; adding thereto the compound of Formula (1) on a batch basis while stirring, with the stirring further continued at room temperature after the addition; subjecting the resulting reaction mixture to solvent removal through rotary evaporation, and extraction and liquid separation with water and dichloromethane to give an organic phase and an aqueous phase which is subjected to extraction with dichloromethane, followed by combination of the organic phases; and subjecting the combined organic phases to be washed with water and then with saturated brine, dried over magnesium sulfate, and isolated by column chromatography using petroleum ether/ethyl acetate (15/1) as eluent to obtain the compound of Formula (4) as a pale yellow oil.

As a particular example, the step (d) may comprise: introducing 40 mL of acetone and then 23 mmol of the compound of Formula (3) into a 100 mL round bottomed flask, which is then placed in an ice bath; adding thereto 27 mmol of the compound of Formula (1) on a batch basis while stirring, with the stirring further continued for 4 hours at room temperature after the addition; subjecting the resulting reaction mixture to solvent removal through rotary evaporation, and extraction and liquid separation with water and dichloromethane to give an organic phase and an aqueous phase which is subjected to extraction with dichloromethane, followed by combination of the organic phases; and subjecting the combined organic phases to be washed with water and then with saturated brine, dried over magnesium sulfate, and isolated by column chromatography using petroleum ether/ethyl acetate (15/1) as eluent to obtain the compound of Formula (4) as a pale yellow oil.

The direct oxidation process, which may be replaced with a peracid oxidation process, in the step (5) may comprise: introducing the compound of Formula (4) into a reaction vessel, followed by addition of 98 wt. % formic acid and 30 wt. % hydrogen peroxide ($H_2O_2$), to conduct a reaction overnight; and subjecting the resulting reaction mixture to solvent removal so as to obtain the target product.

The peracid oxidation process, which may be replaced with a direct oxidation process, in the step (5) may comprise: introducing 98 wt. % formic acid and 30 wt. % $H_2O_2$ into a first reaction vessel to be mixed and stirred for 1 hour at room temperature so as to form a peracid solution; introducing the compound of Formula (4) into a second reaction vessel, into which 98 wt. % formic acid is then introduced to dissolve the compound of Formula (4) therein and which is then placed in an ice bath; and adding thereto dropwise the peracid solution to conduct a reaction overnight after the addition, followed by solvent removal through rotary evaporation, to obtain the target product.

The surfactant produced by the process of the present disclosure has several advantages over prior art surfactants. The surfactant produced by the present process has lower CMC and enables a lower surface tension of a liquid as compared with prior surfactants having two head groups per molecule, thereby enabling the amount of surfactant required and thus the cost to be substantially reduced.

DETAILED DESCRIPTION OF THE EMBODIMENTS

In one example, a surfactant having two head groups and a single tail group per molecule was produced as follows.

(a) Producing a compound of Formula (1) from ethanol and CS₂ according to the following chemical equation (I):

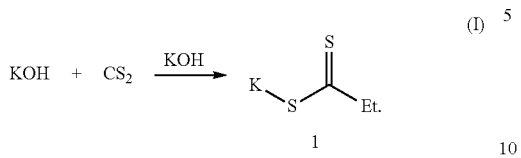
(I)

6 mL of CS₂ and 50 mL of ethanol were introduced into a 150 mL round bottomed flask, which was then placed in an ice bath. 20 mL of a 5 mon aqueous solution of KOH was added thereto while stirring. After the completion of the addition, the stirring was continued for 1.5 hours. Thereafter, the solvent was removed from the resulting reaction mixture through rotary evaporation and the residue was recrystallized from anhydrous ethanol, to obtain the compound of Formula (1), i.e., potassium xanthate, with a yield of 90%.

(b) Producing a compound of Formula (2) from a carboxylic acid (R=C₁₂ alkyl) and Br₂ according to the following chemical equation (II):

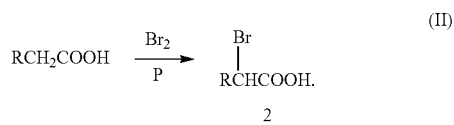
(II)

311 mg of red phosphorus was added to 7.73 mmol of a carboxylic acid (R=C₁₂ alkyl) to form a mixture. The mixture was then heated at 95.9° C. 4.9 g of bromine was added dropwise to the mixture while being heated. The mixture then continued to be heated at 95.9° C. and stirred for 6 hours. Lastly, water was added to the mixture and the mixture was further continually stirred for 20 minutes to give a reaction product. The product was extracted with ether, washed once with each of distilled water and brine, dried over anhydrous MgSO₄, concentrated under reduced pressure, and finally recrystallized from hexane to obtain the compound of Formula (2).

(c) Producing a compound of Formula (3) from the compound of Formula (2) and methanol according to the following chemical equation (III):

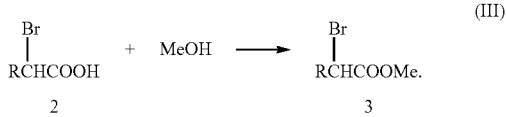
(III)

The compound of Formula (2) was subjected to a reaction with anhydrous methanol at room temperature for 16 hours under nitrogen atmosphere. After the completion of the reaction, methanol was removed from the resulting reaction mixture under a vacuum to obtain the compound of Formula (3).

(d) Producing a compound of Formula (4) from the compound of Formula (1) and the compound of Formula (3) according to the following chemical equation (IV):

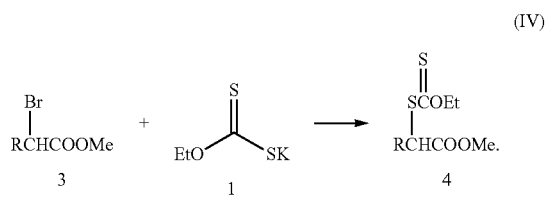
(IV)

40 mL of acetone was introduced into a 100 mL round bottomed flask. 23 mmol of the compound of Formula (3) was then added thereto. The flask was placed in an ice bath. 27 mmol of the compound of Formula (1) was added to the flask in portions. After the completion of the addition, the mixture was stirred at room temperature for 4 hours. Thereafter, the resulting reaction mixture was subjected to solvent removal through rotary evaporation. Water and dichloromethane were added to the residue for extraction and liquid separation to obtain an organic phase and an aqueous phase which was subjected to extraction with dichloromethane. The organic phases were combined, washed with water and then with saturated brine, dried over magnesium sulfate, and isolated by column chromatography using petroleum ether/ethyl acetate (15/1) as eluent to obtain the compound of Formula (4) as a pale yellow oil with a yield of 83.09%.

(e) Producing a compound of Formula (5) from the compound of Formula (4) by a direct oxidation process or by a peracid oxidation process according to the following chemical equation (V):

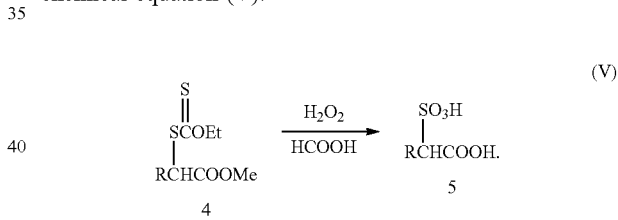
(V)

In this example, we used both the direct oxidation process and the peracid oxidation process to produce the compound of Formula (5).

Direct oxidation process: 1 mmol of the compound of Formula (4) was weighed into a round bottomed flask. 10 mL of 98 wt. % formic acid and 2 mL of 30 wt. % H₂O₂ were added thereto to conduct a reaction overnight. The resulting reaction mixture was subjected to solvent removal through rotary evaporation at 55° C. The residue was washed with chloroform to obtain the compound of Formula (5), which was neutralized with NaOH to obtain a surfactant with two head groups and a single tail group per molecule.

Peracid oxidation process: 10 mL of 98 wt. % formic acid and 2 mL of 30 wt. H₂O₂ were introduced into a round bottomed flask and mixed and stirred at room temperature for 1 hour to form a peracid solution. 1 mmol of the compound of Formula (4) was weighed into another round bottomed flask. 2 mL of formic acid was added thereto to dissolve the compound of Formula (4) therein. The another flask was placed in an ice bath. The peracid solution was added dropwise thereto to conduct a reaction at room temperature overnight after the addition. The resulting reaction mixture was subjected to solvent removal through rotary evaporation at 55° C., washing, and then recrystallization to obtain the compound of Formula (5), which was neutralized with NaOH to obtain a surfactant with two head groups and a single tail group per molecule.

100 mL solutions containing different concentrations of the surfactant obtained in the above example were prepared using conductivity water. An electrical conductivity meter was used to measure the electrical conductivities of the solutions and of the conductivity water used in the preparation of the solutions. The relationship between the electrical conductivity and the surfactant concentration was plotted. The plot showed that the CMC of the surfactant was 0.16 mmol/L.

The surface tension was determined by means of the ring method. The surfactant obtained in the above example was made into solutions having the same surfactant concentration. During the measurement of the surface tension, a ring was slowly immersed in the solutions, and was then slowly lifted with the level of the solution to be lowered relative to the ring and a liquid column formed between the bottom of the ring and the surface of the solution. The liquid column finally broke and was separated from the ring. In this way, the surface tension of the solutions was found to be 7.1 mN/m.

The embodiments discussed above are for explaining the present disclosure by way of example only, and are not to limit the scope of the present disclosure. It is to be understood that various modifications and changes may be made thereto without departing from the scope of the present disclosure. It is also to be understood that it's unnecessary and impossible to provide all possible embodiments of the present disclosure herein, and any modification or change that is obvious from the embodiments discussed herein falls within the scope of the present disclosure as defined by the appended claims.

What is claimed is:

1. A process for producing a surfactant having two head groups and a single tail group per molecule, comprising steps of:
   a. producing a compound of Formula (1) from ethanol and carbon disulfide according to the following chemical equation (I):

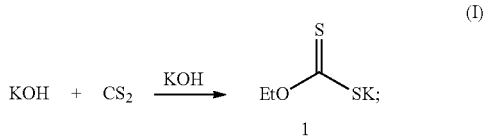

b. producing a compound of Formula (2) from a carboxylic acid and bromine according to the following chemical equation (II):

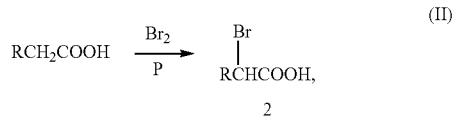

where, R is C12, C14, C16, or C18 alkyl;
   c. producing a compound of Formula (3) from the compound of Formula (2) and methanol according to the following chemical equation (III):

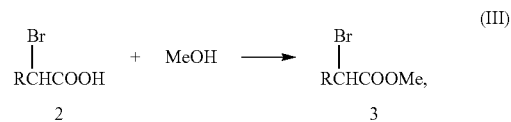

where, R is C12, C14, C16, or C18 alkyl;
   d. producing a compound of Formula (4) from the compound of Formula (1) and the compound of Formula (3) according to the following chemical equation (IV):

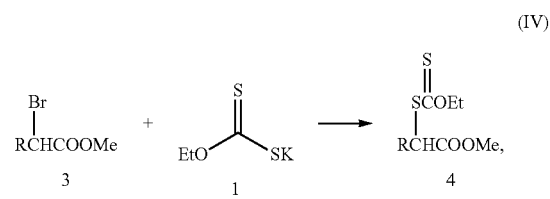

where, R is C12, C14, C16, or C18 alkyl; and
   e. producing a compound of Formula (5) from the compound of Formula (4) by a direct oxidation process or by a peracid oxidation process according to the following chemical equation (V):

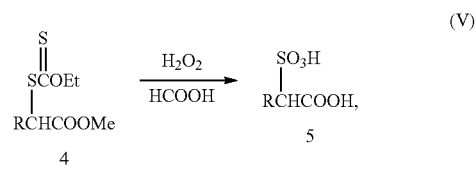

where, R is C12, C14, C16, or C18 alkyl;
   wherein, the compound of Formula (5) obtained is subjected to neutralization treatment with sodium hydroxide to obtain a surfactant having two head groups and a single tail group per molecule.

2. The process of claim 1, wherein, the step (a) comprises: introducing ethanol and carbon disulfide into a reaction vessel, placing the reaction vessel in an ice bath; adding a 5 mol/L aqueous solution of potassium hydroxide to the reaction vessel while stirring, further continuing the stirring after the addition; and
   subjecting the resulting reaction mixture to solvent removal through rotary evaporation and recrystallization from anhydrous ethanol to give the compound of Formula (1).

3. The process of claim 1, wherein, the step (a) comprises: introducing 6 mL of carbon disulfide and 50 mL of ethanol into a 150 mL round bottomed flask, placing the round bottom flask in an ice bath; adding 20 mL of a 5 mol/L aqueous solution of potassium hydroxide to the round bottom flask while stirring, further continuing the stirring for 1.5 hours after the addition; and subjecting the resulting reaction mixture to solvent removal through rotary evaporation and recrystallization from anhydrous ethanol to give the compound of Formula (1).

4. The process of claim 1, wherein, the step (b) comprises: adding red phosphorus to the carboxylic acid to form a mixture, heating the mixture at 95.9° C.; adding bromine dropwise to the mixture while being heated and stirred, further continually heating the mixture at 95.9° C. and stirring after the addition; adding water to the mixture, with the mixture further continually stirred for 20 minutes after the addition of water, to give a reaction product; and extracting the reaction product with ether, washing once with each of distilled water and brine, drying over anhydrous magnesium sulfate ($MgSO_4$), concentrating under reduced pressure, and recrystallizing recrystallized from hexane to obtain the compound of Formula (2).

5. The process of claim 1, wherein, the step (b) comprises: adding 311 mg of red phosphorus to 7.73 mmol of the carboxylic acid to form a mixture, heating the mixture at 95.9° C.; adding 4.9 g of bromine dropwise to the mixture while being heated and stirred, further continually heating the mixture at 95.9° C. and stirring for 6 hours after the addition; adding water to the mixture, with the mixture further continually stirred for 20 minutes after the addition of water, to give a reaction product; and extracting the reaction product with ether, washing once with each of distilled water and brine, drying over anhydrous $MgSO_4$, concentrating under reduced pressure, and recrystallizing from hexane to obtain the compound of Formula (2).

6. The process of claim 1, wherein, the step (c) comprises: subjecting the compound of Formula (2) to a reaction with anhydrous methanol at room temperature for 16 hours under nitrogen atmosphere; and removing methanol from the resulting reaction mixture under a vacuum to obtain the compound of Formula (3).

7. The process of claim 1, wherein, the step (d) comprises: introducing acetone and then the compound of Formula (3) into a reaction vessel, placing the reaction vessel in an ice bath; adding the compound of Formula (1) on a batch basis to the reaction vessel while stirring, further continuing the stirring at room temperature after the addition; subjecting the resulting reaction mixture to solvent removal through rotary evaporation, and extraction and liquid separation with water and dichloromethane to give an organic phase and an aqueous phase which is subjected to extraction with dichloromethane, followed by combination of the organic phases; and washing the combined organic phases with water and then with saturated brine, drying over magnesium sulfate, and isolating by column chromatography using petroleum ether/ethyl acetate (15/1) as eluent to obtain the compound of Formula (4) as a pale yellow oil.

8. The process of claim 1, wherein, the step (d) comprises: introducing 40 mL of acetone and then 23 mmol of the compound of Formula (3) into a 100 mL round bottom flask, placing the round bottom flask in an ice bath; adding 27 mmol of the compound of Formula (1) on a batch basis to the round bottom flask while stirring, further continuing the stirring for 4 hours at room temperature after the addition; subjecting the resulting reaction mixture to solvent removal through rotary evaporation, and extraction and liquid separation with water and dichloromethane to give an organic phase and an aqueous phase which is subjected to extraction with dichloromethane, followed by combination of the organic phases; and washing the combined organic phases with water and then with saturated brine, drying over magnesium sulfate, and isolating by column chromatography using petroleum ether/ethyl acetate (15/1) as eluent to obtain the compound of Formula (4) as a pale yellow oil.

9. The process of claim 1, wherein, the direct oxidation process in the step (e) comprises: introducing the compound of Formula (4) into a reaction vessel, followed by addition of 98 wt. % formic acid and 30 wt. % hydrogen peroxide, to conduct a reaction overnight; and subjecting the resulting reaction mixture to solvent removal to obtain the compound of Formula (5);

and wherein, the peracid oxidation process in the step (e) comprises: introducing 98 wt. % formic acid and 30 wt. % hydrogen peroxide into a first reaction vessel, mixing and stirring for 1 hour at room temperature to form a peracid solution; introducing the compound of Formula (4) into a second reaction vessel, into which 98 wt. % formic acid is then introduced to dissolve the compound of Formula (4), placing the second reaction vessel in an ice bath; and adding to the second reaction vessel dropwise the peracid solution to conduct a reaction overnight after the addition, followed by solvent removal through rotary evaporation, to obtain the compound of Formula (5).

* * * * *